United States Patent [19]

Masuhara et al.

[11] Patent Number: 4,781,913

[45] Date of Patent: Nov. 1, 1988

[54] PHARMACEUTICAL COMPOSITION FOR USE IN DESENSITIZING HYPERSENSITIVE DENTIN

[75] Inventors: Eiichi Masuhara, 2-5-10 Honkomagome, Bunkyo-ku; Hiroyasu Hosoda, both of Tokyo, Japan

[73] Assignee: Eiichi Masuhara, Tokyo, Japan

[21] Appl. No.: 33,242

[22] Filed: Apr. 2, 1987

[30] Foreign Application Priority Data

Apr. 10, 1986 [JP] Japan .................................. 61-82839

[51] Int. Cl.$^4$ ...................... A61K 7/22; A61K 31/615
[52] U.S. Cl. ......................................... 424/54; 514/166
[58] Field of Search ...................... 424/54, 55; 514/166

[56] References Cited

U.S. PATENT DOCUMENTS 4,574,081 3/1986 Shymon .............................. 424/54

FOREIGN PATENT DOCUMENTS

WO81/02672 1/1981 PCT Int'l Appl. ................. 514/166
774107 5/1957 United Kingdom ................ 514/166

OTHER PUBLICATIONS

"Use of Prednisolone in the Elimination of Postoperative Thermal Sensitivity" by J. H. Misteller, D.D.S., *J. Pros. Den.*, vol. 12, No. 6, pp. 1176–1179.

*Primary Examiner*—Douglas W. Robinson
*Attorney, Agent, or Firm*—Nixon & Vanderhye

[57] ABSTRACT

Disclosed is a pharmaceutical composition for use in desensitizing hypersensitive dentin or eliminating odontalgia comprising N-methacryloyl aminosalicylic acid as an active ingredient. The composition may further include an unsaturated compound and a polymerization initiator optionally for retaining the densensitizing effect.

4 Claims, No Drawings

PHARMACEUTICAL COMPOSITION FOR USE IN DESENSITIZING HYPERSENSITIVE DENTIN

The present invention relates to a pharmaceutical composition containing N-methacryloyl aminosalicylic acid which is capable of desensitizing hypersensitive dentin or eliminating odontalgia or toothache, to a method of treating the same and to use of N-methacryloyl aminosalicylic acid in preparing the pharmaceutical composition.

If a part of enamel is cracked or broken as a result of caries or trauma, endodontium will be tremendously hypersensitive to an exgenic stimulus transmitted directly through dentin. Accordingly, a patient suffering from such wound will often feel an acute pain when his affected tooth is just in contact with cold water or air. Particularly, a patient suffering from the odontalgia at the neck of a tooth, where an enamel layer is very thin and is therefore liable to be broken, would be sometimes not able to eat or drink due to a violent toothache.

It has been found in the present invention that N-methacryloyl aminosalicylic acid has an excellent desensitizing activity. The invention provides a pharmaceutical composition for use in desensitizing hypersensitive dentin or eliminating odontalgia caused by, for example, the exgenic stimulus, caries or erosion, which comprises an effective amount of N-methacryloyl aminosalicylic acid and a pharmaceutically acceptable carrier or diluent.

N-methacryloyl aminosalicylic acid, referred to hereinafter as NMSA, an effective ingredient of the pharmaceutical composition according to the present invention, consists of aminosalicylic acid moiety and methacryl moiety, both being linked with each other via amide group. NMSA may be prepared in a conventional manner in which methacryl chloride is reacted with aminosalicylic acid followed by recrystallization in a mixed solvent of ethyl acetate and acetone. NMSA is hardly soluble in water and has little toxicity. Preferred NMSA is N-methacryloyl 5-aminosalicylic acid (5-NMSA).

For the pharmaceutically acceptable carrier or diluent according to the present invention, any liquid carrier known in the art can be used provided that the effective amount of NMSA may be dissolved therein. Such carrier or diluent includes, for example, acetone, ethyl alcohol, ethyl acetate and methyl methacrylate, acetone being preferred among them. NMSA may be contained preferably in an amount of from 0.5 to 20%, more preferably 1 to 15%, most preferably 2 to 10% by weight of the pharmaceutical composition.

The desensitizing composition of the invention may be directly applied to an exposed dentin in a liquid form.

The present invention also relates to a pharmaceutical composition for use in desensitizing the hypersensitive dentin or eliminating the odontalgia, which comprises a compound having an unsaturated group and a polymerization initiator in addition to NMSA and the carrier or diluent mentioned in the foregoing.

While the former composition containing NMSA and the carrier or diluent is rapidly and temporarily effective in the desensitization, the composition containing additionally the unsaturated compound and the initiator may prolong the desensitizing effect far more by copolymerizing the active NMSA with the unsaturated compound.

The term "a compound having an unsaturated group" in the context of the present invention means any compound which is pharmaceutically acceptable and can be copolymerized with NMSA. Preferred example thereof is the compound having methacryl group such as methacrylate, dimethacrylate, trimethacrylate, tetramethacrylate and polymer thereof molecular weight of which is generally of from 10,000 to 1,000,000, and a mixture thereof. Methyl methacrylate, triethyleneglycol dimethacrylate and their polymers are more preferably included in the pharmaceutical composition. Some kinds of carrier or diluent, for example methyl methacrylate, can also serve as the compound having the unsaturated group.

As the polymerization initiator any polymerization initiator included in a known polymerization method such as a redox system or photochemical sensitization system may be contained in the pharmaceutical composition. By way of example, mention may be made of peroxide, tertiary amine, tertiary boron e.g. TBBO and camphor quinone.

The compound having the unsaturated group may be mixed preferably in an amount of from 0.1 to 99%, more preferably 1 to 15%, most preferably 2 to 10% by weight of the pharmaceutical composition. The polymerization initiator may be contained in a suitable amount, generally from 0.01 to 1.0% by weight of the pharmaceutical composition. The selection of the polymerization initiator may be optionally made by those skilled in the art.

The pharmaceutical composition of this type should be stored until use in cold or dark place in order to prevent the occurrence of the copolymerization prior to the application.

The present invention further includes a method of reating the hypersensitive dentin or odontalgia, which comprises applying to the surface of an exposed dentin the pharmaceutical composition according to the present invention.

The above application of the pharmaceutical composition of the present invention is performed, for example, by impregnating a suitable medium such as sponge or sanitary cotton with a proper amount of the composition and using it. The suitable dosage may be determined by those skilled in the art based on a professional experience.

When applied, NMSA in the pharmaceutical composition will promptly interrupt the exgenic stimulus and advantageously demonstrate a remarkable desensitizing effect.

Furthermore, when the pharmaceutical composition containing the compound having the unsaturated group and the polymerization initiator is applied, the above desensitizing effect may be kept for a long time because NMSA can be retained on the surface of the applied dentin as the component of a membrane formed as a result of the copolymerization initiated by a free radical produced by irradiation of light or oxidation and reduction.

Further, when methyl methacrylate-type adhesive resin commercially available is pressed on the surface of the affected dentin after coating with the pharmaceutical composition according to the present invention, the resin will so tight adhere to the dentin via NMSA as to show an adhesive strength of about 170 kg/cm$^2$. Toothache, on the other hand, may leave off endodontium very quickly.

Alternatively, after the pharmaceutical composition containing the compound having the unsaturated group and the polymerization initiator is applied and cured on the surface of the affected dentin, a polyfunctional methacrylate type composite resin also commercially available may be pressed and cured on the previously cured composition so as to obtain an adhesive strength of about 150 kg/cm$^2$ as well as the elimination of the toothache at endodontium.

As seen from the above, the pharmaceutical composition according to the present invention can show the rapid and continuous desensitizing effect only by applying it on the surface of the exposed dentin. In addition, it may also serve as the effective adhesive which may bind the dentin and adhesive resin (synthetic resin) or repairing composite resin together. Thus, the pharmaceutical composition of the present invention provides a great progress in the dental therapy of caries and the like.

In a further aspect of the present invention, there is provided use of NMSA for the preparation of the pharmaceutical composition for use in desensitizing hypersensitizing dentin or odontalgia.

The following examples illustrate the invention but are not construed as limiting the scope of the claims hereinunder mentioned.

EXAMPLE 1

A piece of sponge (2×2×2 mm) was sufficiently impregnated with the pharmaceutical composition comprising 95 parts by weight of acetone and 2 parts by weight of 5-NMSA. When the hypersensitive dentin due to endodontitis in an early stage had been coated with the above composition in a thin layer by means of the sponge, the odontalgia was instantly eliminated.

EXAMPLE 2

The pharmaceutical composition comprising 96 parts by weight of methyl methacrylate, 2 parts by weight of 5-NMSA and 0.01ml of tri-n-butyl borane (TBBO) as the polymerization initiator at an ambient temperature was immediately absorbed into a small piece of sponge and applied to the surface of a prepared cavity formed at a vital tooth in an operation. The composition penetrated into dental canaliculi and was then copolymerized and cured a few minutes later so as to form a polymeric membrane on the surface of the cavity. By this treatment the toothache at the above prepared cavity was immediately mitigated. Furthermore the desensitizing activity of the applied composition could remain for a long time as a result of the formation of the membrane, which could, on the other hand, protect the endodontium.

EXAMPLE 3

The pharmaceutical composition according to the present invention in a form of slurry paste was prepared by adding 0.01ml of TBBO to a mixture (0.7ml) of 98 parts by weight of methyl methacrylate and 2 parts by weight of 5-NMSA followed by the incorporation of polymethyl methacrylate in a fine powder (1 mg). The same treatment as in EXAMPLE 2 was performed with this pharmaceutical composition so as to obtain the excellent desensitizing effect as described in EXAMPLE 2. The cured composition firmly adhered to the dentin with an adhesive strength of 170 kg/cm$^2$.

When a commercially available repairing composite resin was further pressed on the surface of the cured composition resin, both resins were tightly bound with each other through chemical bond, providing the affected tooth with an aesthetic repair as well as the continuous desensitizing effect.

EXAMPLE 4

The pharmaceutical composition according to the present invention was prepared by mixing 60 parts by weight of methyl methacrylate, 37 parts by weight of triethylene glycol dimethacrylate, 2 parts by weight of 5-NMSA and one part by weight of camphor quinone as a photo-polymerization initiator (photochemical sensitization agent) at an ambient temperature and stored in a vessel shielded from light. After the application of the pharmaceutical composition thus prepared by means of a small piece of sponge on the surface of the exposed dentin due to caries or erosion, it was irradiated with light at 400 to 600 nm for 40 sec to cure the composition. The cured membrane of the pharmaceutical composition rapidly interrupted the exgenic stimulus and had the continuous activity of mitigating odontalgia.

When photo-polymerization type resin paste was further pressed on the thus cured membrane and irradiated with a visible light for 30 sec, the resin paste was cured and bound very firmly with the cured membrane via chemical bond. In such case, the aesthetic repair was obtained as well as the continuous desensitizing effect on the odontalgia due to the exgenic stimulus towards endodontium.

What is claimed is:

1. A dental compositon comprising an effective amount for use in desensitizing hypersensitive dentin or eliminating odontalgia in a patient in need thereof of N-methacryloyl aminoscàlicylic acid and a pharmaceutically acceptable carrier or diluent therefor.

2. A pharmaceutical composition of claim 1 wherein the N-methacryloyl aminosalicylic acid is N-methacryloyl 5-aminosalicylic acid.

3. A pharmaceutical composition of claim 2 wherein the carrier or diluent is selected from the group consisting of acetone, ethyl alcohol, ethyl acetate and methyl methacrylate.

4. A method of desensitizing hypersensitive dentin or eliminating odontalgia in a patient in need thereof which comprises applying to the surface of an exposed dentin the composition of claim 1 in a therapeutically effective amount.

* * * * *